US00PP12916P2

(12) United States Plant Patent
Olesen et al.

(10) Patent No.: US PP12,916 P2
(45) Date of Patent: Sep. 3, 2002

(54) MINIATURE ROSE PLANT NAMED 'POULELE'

(76) Inventors: L. Pernille Olesen; Mogens N. Olesen, both of Hillerødvejen 49, Fredensborg DK-3480 (DK)

( * ) Notice: Subject to any disclaimer, the term of this patent is extended or adjusted under 35 U.S.C. 154(b) by 8 days.

(21) Appl. No.: 09/655,261

(22) Filed: Sep. 5, 2000

(51) Int. Cl.[7] ..... A01H 5/00

(52) U.S. Cl. ..... Plt./121

(58) Field of Search ..... Plt./121, 122, 116

(56) References Cited

PUBLICATIONS

UPOV–ROM GTITM Computer Database 2001/02, Apr. 2, 2001, GTI Jouve Retrieval Software, Citation for Rosa 'Poulele'.*

Community Plant Variety Office "Certificate on the Grant ... " 6 Pages. Jun. 19, 2000 EU.

* cited by examiner

*Primary Examiner*—Bruce R. Campell
*Assistant Examiner*—June Hwu

(57) ABSTRACT

A new miniature rose plant which has abundant hot-pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present discovery constitutes a new and distinct variety of a miniature rose plant which was discovered in a cultivated area in Fredensborg, Denmark. The mutation resulted from 'POULrac', a miniature pot rose hybridized by the same inventors, which is the subject of U.S. Plant Pat. No. 11,543, issued on Oct. 3, 2000. The new rose variety resulted from a naturally occurring mutation of unknown causation on a branch of 'POULrac'.

The antecedent cultivar 'POULrac' has red flowers while 'POULele' has hot-pink flowers.

The rose plant of the present discovery has a unique combination of characteristics which are outstanding in the new variety and which distinguish it from the original rose 'POULrac' as well as all other varieties which we are aware of. For example, the new variety has:

. Abundant, hot-pink, double flowers;

. Vigorous and compact growth;

. Year-round flowering under glasshouse conditions;

. Suitability for production from softwood cuttings in pots;

. Durable flowers and foliage which make the variety suitable for distribution in the floral industry.

The combination of qualities of this variety represents significant improvement over previously available commercial cultivars of this type and distinguishes 'POULele' from all other varieties of which we are aware. As part of their rose development program, L. Pernille Olesen and Mogens N. Olesen germinated the seeds from the aforementioned discovery and conducted evaluations on the resulting seedlings in a controlled environment in Fredensborg, Denmark, in May of 1998.

Asexual reproduction of 'POULele' by cuttings and traditional budding was first done by L. Pernille and Mogens N. Olesen in Fredensborg, Denmark in October of 1998. This initial and other subsequent propagations conducted in controlled environments have demonstrated that the characteristics of 'POULele' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULele'. Specifically illustrated in SHEET 1:

1. Flowering stem showing branch and the attachment of leaves, bud, and peduncle;
2. Flower bud, partially opened bud, and open bloom;
3. Flower petals, detached;
4. Sepals, receptacle, and pedicel;
5. A bare stem exhibiting thorns;
6. Leaves.

DETAILED DESCRIPTION OF THE VARIETY

The following is a description of 'POULele', as observed in its growth in glasshouses in Half Moon Bay, Calif., on plants aged 16 weeks. Color references are made using The Royal Horticultural Society (London, England) Colour Chart, 1995, except where common terms of color are used.

For a comparison, several physical characteristics of the rose variety 'POULrac', a miniature rose variety from the same inventors described and illustrated in U.S. Plant Pat. No. 11,543 dated Oct. 3, 2000, are compared to 'POULele' in Chart 1.

CHART 1

| | 'POULele' | 'POULrac' |
|---|---|---|
| Petal Color, Upper Surface: | Red-Purple Group 57A. | Red Group 46A with intonations of Red-Purple Group 60B. |

CHART 1-continued

| | 'POULele' | 'POULrac' |
|---|---|---|
| Petal Color, Reverse Surface: | Red-Purple Group 57B. | Red Group 46A. |
| Petalage: | Double; 34 to 36 Petals. | Double; 35 to 40 petals. |

Parents: Mutation of 'POULrac'.

Classification:

*Botanical.*—*Rosa hybrida.*

*Commercial.*—Miniature.

FLOWER AND FLOWER BUD

Blooming habit: Recurrent.

Flower bud:

*Size.*—Upon opening, 13 mm–15 mm in length from base of receptacle to end of bud.

*Bud form.*—Short, pointed ovoid.

*Bud color.*—As sepals unfold Red-Purple Group 57A, Red-Purple Group 57A at ¼ opening.

*Sepals.*—Sepal length is 15 mm; Sepal width is 8 mm. Green Group 143C, with a striation of Yellow Green Group 144B. Somewhat weak foliaceous appendages on three of the five sepals. Surfaces of sepals moderately pubescent. Stipitate glands are present on edges of sepals.

*Receptacle.*—Surface: Smooth. Shape: Funnel shaped. Size: 7 mm (h)×7 mm (w). Color: Yellow-Green Group 144A.

*Peduncle.*—Surface: Sparsely arrayed with stipitate glands. Length: 22 to 30 mm average length. Color: Yellow-Green Group 144A. Strength: Upright.

*Borne.*—Generally with 3 to 4 buds per flowering stem.

Flower bloom:

*Fragrance.*—None.

*Duration.*—As a pot plant, flowers last from 7 to 9 days. As a cut flower 3 to 4 days.

*Size.*—Small for a 10 cm pot rose. Average flower diameter is 35 mm when open.

*Form.*—Shape of flower when viewed from the side: Upon opening, upper part: Flattened convex. Upon opening, lower part: Flattened convex. Open flower, upper part: Flattened convex. Open flower, lower part: Flattened convex.

*Petalage.*—Average range: 34 to 36 petals under normal conditions with 2 to 3 petaloids.

Color:

*Upon opening, petals.*—Outermost petals: Upper Surface: Red-Purple Group 57A. Reverse Side: Red-Purple Group 57C. Innermost petals: Upper Surface: Red-Purple Group 57A. Reverse Side: Red-Purple Group 57B.

*Upon opening, basal petal spots.*—Outermost petals: Outer Side: White Group 155C. Inner Side: White Group 155C. Innermost petals: Outer Side: Greyed-Yellow Group 160C. Inner Side: Greyed-Yellow Group 160C.

*After opening, petals.*—Outermost petals: Upper Surface: Basal Zone, Red-Purple Group 57A; Middle Zone Red-Purple Group 57B, Marginal Zone Red-Purple Group 57C. Reverse Side: Basal Zone, Red-Purple Group 57A; Middle Zone Red-Purple Group 57B, Marginal Zone Red-Purple Group 57C. Innermost petals: Upper Surface: Red-Purple Group 57A with intonations of Red-Purple Group 57B/C. Reverse Side: Red-Purple Group 57C with intonations of Red-Purple Group 57A/B.

*After opening, basal petal spots.*—Outermost petals: Outer Side: White Group 155C with intonations of 160C. Inner Side: White Group 155C with intonations of 160C. Innermost petals: Outer Side: White Group 155C with intonations of Greyed-Yellow Group 160C. Inner Side: White Group 155C with intonations of Greyed-Yellow Group 160C.

General tonality: On open flower Red-Purple Group 57A. No change in the general tonality at the end of the 8th day. Afterwards, general tonality is Red-Purple Group 66C/D.

*Petals.*—Petal Reflex: Petals reflex moderately. Petal Edge: With point in center of margin. Shape: Deltoid. Petaloids: 2 to 3. Petaloids are approximately 5 to 7 mm wide and 8 to 12 mm long. Thickness: Medium thickness. Texture: Satiny. Arrangement: Imbricated.

Reproductive organs:

*Pollen.*—Color: Yellow-Orange Group 15A. Abundance: Average.

*Anthers.*—Size: 2 mm long. Color: Yellow-Orange Group 15D. Abundance: 30 to 35.

*Filaments.*—Color: Yellow Group 12A. Length: 3 to 4 mm.

*Stigmas.*—Position: Slightly superior relative to anthers. Color: Greyed-Yellow Group 160D.

*Styles.*—Color: Yellow-Green Group 145D; Red-Purple Group 66A immediately below Stigma. Length: 5 to 6 mm. Quantity: 25 to 30.

*Hips.*—None observed.

PLANT

Plant growth: Vigorous, compact. When grown as a 10 cm pot plant, the average height of the plant itself is 27 cm and the average width is 25 cm.

Stems:

*Color.*—Young wood: Yellow-Green Group 144A. Older wood: Yellow-Green Group 144A.

*Prickles.*—Incidence: Moderate. Size: Average length: 33 mm–5 mm. Color: Greyed-Yellow 160A. Shape: Linear.

*Surface.*—Young wood: Smooth. Older wood: Smooth.

Plant foliage: Normal number of leaflets on leaves in middle of the stem: 5 leaflets.

*Leaf size.*—29 mm (l)×18 mm (w).

*Abundance.*—Average.

*Color.*—Upper Leaf Surface: Green Group 137A. Lower Leaf Surface: Green Group 138B. Juvenile foliage: Green Group 137A.

Plant leaves and leaflets:

*Stipules.*—Size: 10 mm–11 mm. Color: Green Group 137A with intonations of Green Group 138B.

*Stipitate glands.*—Present on reflexed edge of stipule.

*Petiole.*—Length: 8 mm–10 mm. Color: Green Group 138C. Underneath: Yellow-Green Group 144A; limited numbers of stipitate glands. Margins: Yellow-Green Group 144A.

*Rachis.*—Color: Green Group 138B. Underneath: Yellow-Green Group 144A. Margins: Yellow-Green Group 144A.

*Leaflet.*—Edge: Serrated. Shape: Ovate. The leaflet's apex is acuminate. The leaflet's base is rounded. Texture: Moderately glossy, thin.

Disease resistance: Average resistance to mildew, black spot, and Botrytis under normal growing conditions in Half Moon Bay, Calif.

Cold hardiness: 'POULele' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant flowers, vigorous and compact growth, year round flowering under glasshouse conditions, suitability for production from softwood cuttings in pots, and durable flowers and foliage which make the variety suitable for distribution in the floral industry.

* * * * *

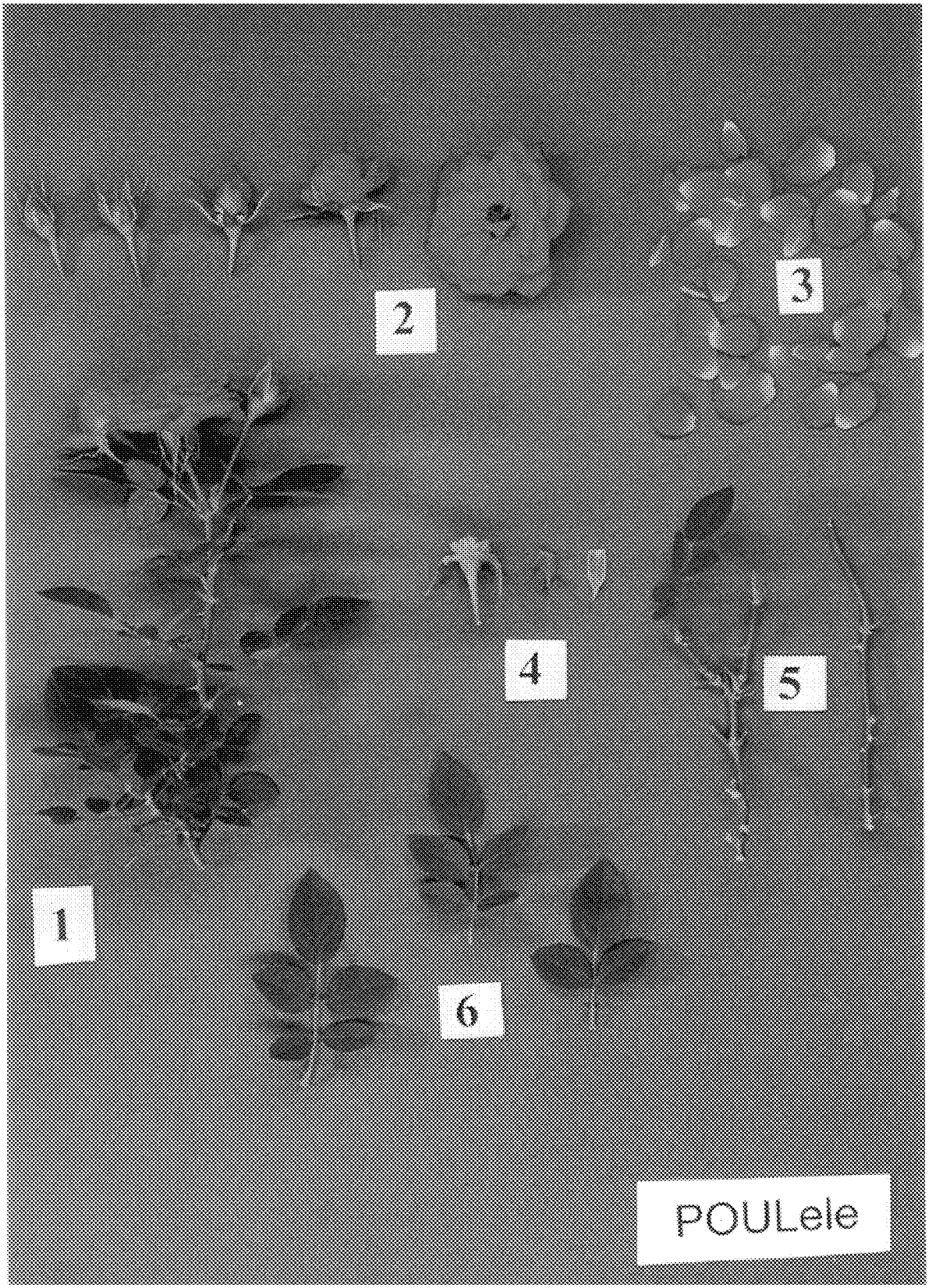
1
2
3
4
5
6
POULele